United States Patent
Schiebahn et al.

(10) Patent No.: US 10,242,566 B2
(45) Date of Patent: Mar. 26, 2019

(54) PERSONAL HYGIENE SYSTEM

(71) Applicant: Braun GmbH, Kronberg (DE)

(72) Inventors: Matthias Schiebahn, Bad Camberg (DE); Leo Faranda, Rodgau (DE); Ingo Vetter, Karben (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/197,409

(22) Filed: Jun. 29, 2016

(65) Prior Publication Data
US 2017/0004703 A1    Jan. 5, 2017

(30) Foreign Application Priority Data

Jun. 30, 2015  (EP) .................................... 15174465

(51) Int. Cl.
*G08C 19/00*    (2006.01)
*A46B 15/00*    (2006.01)
(Continued)

(52) U.S. Cl.
CPC ................ *G08C 19/00* (2013.01); *A46B 9/04* (2013.01); *A46B 15/0004* (2013.01);
(Continued)

(58) Field of Classification Search
CPC .............. A61C 17/221; A61C 17/3409; G01D 5/24452; G01D 5/2449; G06F 19/34;
(Continued)

(56) References Cited

U.S. PATENT DOCUMENTS 7,976,388 B2 * 7/2011 Park ................... A46B 15/0002
  15/105
8,683,635 B2 * 4/2014 Jungnickel ........... A61C 17/221
  15/22.1

(Continued)

FOREIGN PATENT DOCUMENTS

WO    WO2014016718    1/2014

OTHER PUBLICATIONS

European Search Report, dated Dec. 2, 2015; 5 pages.

*Primary Examiner* — Yong Hang Jiang
(74) *Attorney, Agent, or Firm* — Parker D. McCrary; Vladimir Vitenberg

(57) ABSTRACT

A personal hygiene system includes a personal hygiene device having a receiver unit, a control unit, and a functional unit; and a separate control device having a transmitter unit. The control unit drives the functional unit in at least one of a first functional mode and a second functional mode different from the first functional mode. The control unit inhibits provision of the second functional mode while the control unit is in a default state. The transmitter unit sends at least a first signal to the receiver unit of the personal hygiene device when the separate control device is switched from a default control mode to a first control mode. The control unit can be switched from the default state into a first state when the first signal is received by the receiver unit, in which first state the control unit permits provision of the second functional mode at least during a first allowance period.

13 Claims, 2 Drawing Sheets

(51) Int. Cl.
    *A61C 17/34*     (2006.01)
    *A46B 9/04*     (2006.01)
    *A61C 17/22*     (2006.01)
    *G06F 19/00*     (2018.01)
    *G06Q 30/06*     (2012.01)

(52) U.S. Cl.
    CPC ........ *A46B 15/004* (2013.01); *A46B 15/0012* (2013.01); *A61C 17/221* (2013.01); *A61C 17/3409* (2013.01); *G06F 19/34* (2013.01); *G06Q 30/06* (2013.01); *A46B 2200/1066* (2013.01)

(58) Field of Classification Search
    CPC ...... G06Q 30/06; G08C 19/00; H02K 11/215; A46B 15/0004; A46B 15/0012; A46B 15/004; A46B 2200/1066; A46B 9/04
    See application file for complete search history.

(56) References Cited

U.S. PATENT DOCUMENTS

| | | | |
|---|---|---|---|
| 2006/0123570 A1 | 6/2006 | Pace et al. | |
| 2009/0143914 A1* | 6/2009 | Cook | A46B 15/0002 700/275 |
| 2015/0230899 A1* | 8/2015 | Vetter | A46B 15/0004 700/90 |
| 2016/0143718 A1 | 5/2016 | Serval et al. | |

* cited by examiner

PERSONAL HYGIENE SYSTEM

FIELD OF THE INVENTION

The present invention is concerned with a personal hygiene system comprising a personal hygiene device and a separate control device and it is in particular concerned with controlling functional modes to be provided by the personal hygiene device.

BACKGROUND OF THE INVENTION

It is known that a personal hygiene system can comprise a personal hygiene device (e.g. an electric toothbrush) and a separate control device (e.g. a smart phone on which a particular mobile app is installed). It is known that a separate control device can be used to control some characteristics of the personal hygiene device, e.g. to disable functional modes of the personal hygiene device or to change the order of the functional modes that can be chosen via a mode switch on the personal hygiene device.

It is an object of the present disclosure to provide a personal hygiene system that is improved over the known personal hygiene systems or that represents at least an alternative.

SUMMARY OF THE INVENTION

In accordance with one aspect there is provided a personal hygiene system comprising a personal hygiene device having a receiver unit, a control unit and a functional unit, and a separate control device having a transmitter unit. The control unit is arranged to drive the functional unit in at least a first functional mode and a second functional mode different to the first functional mode and the control unit is further arranged to inhibit provision of the second functional mode while the control unit is in a default state and the transmitter unit of the separate control device is arranged to send at least a first signal to the receiver unit of the personal hygiene device when the separate control device is switched from a default control mode to a first control mode. Further, the control unit is arranged to be switched from the default state into a first state when the first signal is received by the receiver unit, in which first state the control unit is arranged to permit provision of the second functional mode at least during a first allowance period.

BRIEF DESCRIPTION OF THE DRAWINGS

The present disclosure will be further elucidated by a detailed description of example embodiments and with reference to figures. In the figures

DETAILED DESCRIPTION OF THE INVENTION

Figure 1:
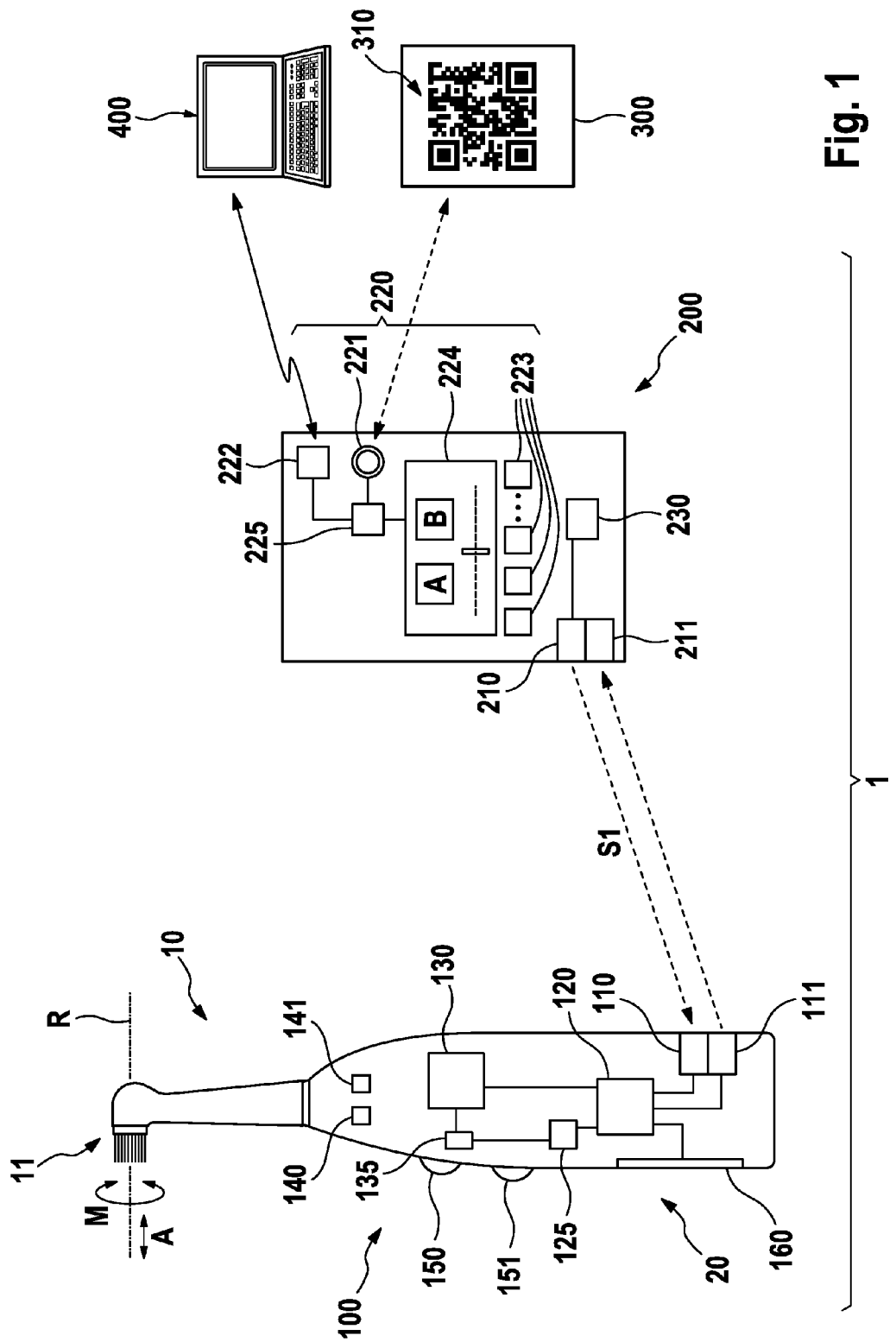
FIG. 1 is a schematic depiction of a personal hygiene system comprising a personal hygiene device and a separate control device.

The present disclosure is concerned with a personal hygiene system comprising a personal hygiene device and a separate control device. In simple words, the personal hygiene device is arranged to be able to provide two different functional modes via a functional unit that is controlled by a control unit. This shall mean that the control unit is structured such that it can control the functional unit to provide a first functional mode, which is the default mode of the personal hygiene device, and it can control the functional unit to provide a second functional mode. In the default state, the control unit is arranged to inhibit the provision of the second functional mode. E.g. the personal hygiene device may have a mode switch by which the functional mode provided by the functional unit can be altered, but in the default mode, pushing the mode switch would not change the mode that is provided as only the first functional mode is permitted. It is noted here that it is not necessary that the control unit has driving information available for controlling the functional unit to provide the second functional mode when it is in its default state, but just that the control unit has a structure that in principle allows switching between the provision of a first functional mode and of a second functional mode different to the first functional mode and a structure that in principle allows controlling the functional unit to provide the first and second functional mode. Notwithstanding the just made statement, in some embodiments, the control unit comprises driving information for controlling the functional unit to provide the second functional mode, e.g. the control unit may comprise a memory unit in which such driving information is stored. In a non-limiting example, the personal hygiene device is an electric toothbrush and the functional unit comprises a drive (e.g. a motor with a drive shaft, where the drive shaft may be coupled to the motor via a gear) for driving a functional head (here: toothbrush head) into a given motion (i.e. a first functional mode), e.g. an oscillating rotation provided at a certain first frequency and with a certain first amplitude. A second functional mode may then be provided by driving the functional head into a different motion, e.g. the frequency of the oscillating rotation may be changed, the amplitude may be changed or amplitude and/or frequency may be time-dependent. Or in the second functional mode a further motion component may be added such as a poking motion in the direction of the rotation axis around which the oscillating rotation occurs. Alternatively or additionally, further motion parameters may be changed for the second functional mode in comparison to the first functional mode. Generally, the functional unit may be any unit that provides a function of the personal hygiene device, e.g. a display unit, an audio and/or video unit, an illumination unit (such as at least one LED), a haptic response unit, a sensor unit etc. The functional unit may also be a combination of at least two such units (which then form sub-units of the functional unit), e.g. the functional unit may comprise a drive unit as a first sub-unit and a display unit as a second sub-unit.

Generally, the personal hygiene device may comprise a treatment head for providing a personal hygiene treatment (e.g. a brush head as just described, a massage head, a hair removing head etc.) and the functional unit may then be coupled with the treatment head to drive the treatment head into a functional mode.

The control unit is enabled to control the functional unit to provide the second functional mode once the control unit is switched from the default state into a first state. In some embodiments, switching the control unit from the default state into the first state comprises providing the necessary information for enabling the control unit to control the functional unit to provide the second functional mode.

The personal hygiene system is arranged to provide the second functional mode at least during a first allowance period. The first allowance period may be an absolute time span such as three hours, one day (24 hours), two weeks, three month etc. after the control unit was switched into the first state. The control unit may then automatically switch back into the default state when the first allowance period has passed. In some embodiments, the first allowance time is a relative time span, e.g. 10 minutes, 1 hour, 5 hours etc. of using the second functional mode.

In some embodiments, the control unit is arranged to inhibit provision of the first functional mode while the control unit is in the first state.

Generally, the personal hygiene device may have more than one permitted functional mode in the default state of the control unit, e.g. the control unit may be arranged to control the functional unit to provide the first functional mode and to provide a further functional mode different to the first functional mode and different to the second functional mode. In some embodiments, the control unit may permit three, four, five etc. different functional modes while being in the default state. Further, the control unit may be arranged to permit not only a second functional mode when it is in the first state but also a further functional mode that is different to the first functional mode (and different to any other functional mode that may be permitted in the default state) and different to the second functional mode. In some embodiments, the control unit can additionally be switched into a second state or even further states. In such a second state (or a further state), the control unit may be arranged to permit at least a third functional mode that is different to the first functional mode and to the second functional mode. The third functional mode may then be permitted for a second allowance period that may be identical or different in length to the first allowance period and the first and second allowance periods may at least partially overlap. In some embodiments, the control unit is arranged to control the functional unit to provide a first, a second and a third functional mode, but only the first functional mode is permitted in the default state. Then, the modes permitted in a first and a second state may be chosen from the list of available functional modes, e.g. the second functional mode is enabled in the first state and the second and the third functional modes are enabled in the second state. In such embodiments, different subsets of available functional modes are enabled in the different states of the control unit.

In some embodiments, the functional unit comprises at least two sub-units (e.g. a drive unit and a sensor unit) and the first mode then comprises a disabled second sub-unit, while the second sub-unit is enabled in the second mode without necessarily changing the way the first sub-unit is controlled (e.g. in the second mode a drive unit provides the same driving as in the first mode but a sensor unit is switched on in the second mode and provides, e.g., information about the quality of the hygiene treatment such as amount of residual plaque on a currently treated tooth surface). The first and second functional modes (and any other functional mode) may then each be a different combination of modes of the sub-units.

In accordance with the present disclosure, the separate control device is arranged to switch the control unit from the default state to the first state. In order to do so, the separate control device is arranged to send a first signal via a transmitter unit to a receiver unit of the personal hygiene device. The separate control device may be arranged to send the first signal after it is switched from a default control mode into a first control mode. As will be explained in more detail further below, the switching of the separate control device from its default control mode into the first control mode may be triggered when the separate control device receives a first instruction command that is identical to (i.e. coincides with) a predetermined instruction command It is noted that the separate control device does not need to be arranged to send the first signal immediately after the separate control device is switched from the default control mode to the first control mode. E.g. the separate control device may be arranged to postpone sending the first signal until a further condition is met. This will be explained in more detail further below. As was explained for the personal hygiene device, the separate control device may additionally be switched into a second control mode etc. in which it sends another signal to the personal hygiene device by which the control unit is switched, e.g., into the above discussed second state etc.

The first signal may comprise only a flag that indicates that the second functional mode is to be enabled. In some embodiments, the first signal comprises information about the length of the first allowance time during which the second functional mode is enabled. In some embodiments, the first signal comprises information about the second functional mode (e.g. driving information allowing the control unit to control the functional unit such that it will provide the second functional mode).

The separate control device may be arranged such that it sends (via the transmitter unit) a second signal to the personal hygiene device when a first condition is met. The second signal may then trigger the control unit of the personal hygiene device to un-alterably control the functional unit such that it provides one of the available functional modes. The first condition may be met once the separate control device notices that the personal hygiene device is switched on. E.g. in some embodiments the separate control device may comprise a sound recognition unit that can determine when the personal hygiene device is switched on based on the sound of the switched-on device. In some embodiments, the personal hygiene device comprises a transmitter unit and transmits a third signal to the separate control device once a second condition is met, e.g. when the personal hygiene device is switched on. The separate control device may then be arranged to consider the first condition as met when the third signal is received via a receiver unit of the separate control device.

In some embodiments, the separate control device comprises a storage unit for storing a first signal sequence. The separate control device may be arranged to transmit consecutive members of the first signal sequence each time a third condition is met. In some embodiments, the separate control device is arranged to consider the first condition as met when the third condition is met and the respective next member of the first signal sequence is then send as second signal. The members of the first signal sequence may comprise information about the functional mode to be employed. This allows automatically providing a sequence of personal hygiene treatment operations optimized for a certain target. E.g. the user may have bought an upgrade optimized for whitening teeth (the personal hygiene device being an electric toothbrush) and the separate control device then controls the personal hygiene device such that a sequence of functional modes is used that is optimized for reaching whiter teeth.

A personal hygiene system as described allows that a consumer can buy a "standard" device that only provides a single functional mode and the consumer can upgrade the personal hygiene device further by, e.g., buying an upgrade package at a later stage without the need to buy a different personal hygiene device. As was explained in connection with the first allowance time, also short trial periods for a potential upgrade to a personal hygiene device with at least one further functional mode can be provided, e.g. as a free trial, allowing the consumer to first test a second functional mode before buying a respective upgrade.

A personal hygiene device as described herein may be an electric toothbrush, an electric flossing device, an electric oral irrigator, an electric epilator, an electric massager or exfoliator, an electric shaver or trimmer etc. A separate control device may be a proprietary device particularly provided to control the personal hygiene device or a general purpose device that comprises a particular program for controlling the personal hygiene device, e.g. a smart phone, a tablet computer, a laptop etc. A proprietary "mobile app" may serve as program of a general purpose device such as a smart phone.

In some embodiments, the separate control device comprises an external interface unit that is arranged for receiving at least a first instruction command and the separate control device is then arranged to be switched from the default control mode to the first control mode when the first instruction command coincides with a predetermined instruction command In particular, the external interface unit may comprise at least one of (a) a reader unit arranged for reading at least a portion of the first instruction command from a separate instruction element, (b) a network connection unit arranged for receiving at least a portion of the first instruction command from a distant unit such as a network server, or (c) a user-interface unit that is arranged for receiving user input and for using the user's input at least as a portion of the first instruction command. The external interface unit may comprise a combination of at least two of the previously mentioned units. While in some embodiments at least one of the previously mentioned units is present and arranged to receive the complete first instruction command, in some embodiments, at least two of the units are present and at least two of them are arranged such that each of the units receives one different portion of the first instruction command so that the at least two portions together yield the complete first instruction command The reader unit may be realized by a camera, a (bar code) scanner, an imager, a radio frequency reader, etc., which reader unit may comprise a particular programming to perform as reader unit, e.g. a camera may comprise a particular program for reading and interpreting a QR code.

The network connection unit may comprise a network connection chip for establishing a wired or a wireless connection to a network (e.g. a Local Area Network—LAN—or a wireless LAN (i.e. a WLAN), a WAN etc.) or for a direct connection with the Internet so that a connection with a distant network device (e.g. a distant server unit, e.g. from the supplier of the personal hygiene device) can be enabled.

The user-interface unit may comprise a keyboard and/or a touch sensitive display allowing a user to input information, e.g. an alphanumeric string.

The external interface unit may be used to receive a first instruction command, which first instruction command may then be compared with at least one predetermined instruction command. E.g. the user may buy an upgrade for the personal hygiene device comprising a separate instruction element, e.g. a piece of paper comprising a representation of the first instruction command such as a QR code or an alphanumeric string. The reader device may then be able to read and interpret the representation of the first instruction command to thus determine the first instruction command A user may be able to input the first instruction command (e.g. an alphanumeric string) into the user-interface unit. The separate control unit may then be arranged for comparing the first instruction command with a predetermined instruction code and to switch itself from a default control mode (or its current control mode) into a different control mode (e.g. a first control mode) if the first instruction command coincides with a predetermined instruction command for unlocking the respective control mode. In some embodiments, the comparison is done by a distant network unit such as a distant server. In such an embodiment, the separate control device sends the first instruction command via a network connection unit to the distant network unit, which performs the comparison and sends back a confirmation signal (e.g. together with an information about the control mode into which the separate control device is to be switched; potentially also together with further information about the respective functional mode—e.g. the second functional mode—, e.g. driving information for the second functional mode) or an invalidation signal in case the first instruction command was not valid.

When buying an upgrade package, the consumer may receive a representation of a portion of a first instruction command or a representation of a complete first instruction command. E.g. the upgrade package may comprise a particular replaceable personal hygiene treatment head (e.g. a whitening brush head in case the upgrade package would be concerned with teeth whitening for an electric toothbrush) and a scratch-off portion comprising the representation of (the portion of) the first instruction command hidden under a layer that is to be scratched off (the embodiment with scratch-off layer is just given by way of example and shall not be interpreted as limiting). E.g., as already discussed, the representation of the (portion of the) first instruction command may be an alphanumeric string, a bar code, a QR code etc., which can be read (after the scratch-off layer is removed) by e.g. a reader unit. In some embodiments, one portion of the first instruction command is provided via the upgrade package and another portion may be provided together with the personal hygiene device, e.g. as a loose insert or as part of the product leaflet (e.g. another portion of the first and even of further instruction commands may be provided as an alphanumeric code or bar code etc. via a printed representation in the product leaflet). In order to set the separate control device into the first control mode, the user may then need to read a first portion of the first instruction command from the upgrade package via a reader unit and another portion may need to be entered via a user-interface unit.

The separate control device may comprise an input element (e.g. a button) by which a receiving operation of the external interface unit (e.g. a reading operation by the reader unit such as a picture taken by a camera) is triggered.

The personal hygiene system may comprise an indicator element (e.g. an LED) for indicating at least the availability of a second functional mode.

In some embodiments, the personal hygiene system comprises a display (e.g. realized at the personal hygiene device or at the separate control device). The display may then be arranged to display certain hints or information, such as displaying the name of toothpaste that should optimally be used together with the current functional mode or a hint that flossing should be applied after the tooth brushing operation.

In some embodiments, the separate control device or the control unit are arranged to set at least one parameter of at least the second functional mode in dependence on use information of the personal hygiene device. E.g. the personal hygiene system may comprise a timer that measures the typical use time of a given user per personal hygiene treatment as the respective parameter of the second functional mode. If this time span is in average higher or lower than the length of the default treatment time, the default treatment time as the respective parameter of the second functional mode may be reset to the average treatment time employed by the given user.

In some embodiments, the personal hygiene device comprises at least a first sensor unit for monitoring at least one use parameter (e.g. such a use parameter may be the pressure with which a head of the personal hygiene device is pushed against the treatment zone; e.g. the treatment head may be a brush head and the treatment zone is then the teeth of the user). The personal hygiene system may be arranged to set at least one parameter of the second functional mode in dependence on the use information generated by the first sensor unit. E.g. if the use parameter is the applied pressure, the duration as the respective parameter of the second functional mode may be set in dependence on the applied pressure. E.g. too less applied pressure may lead to an increase of the default treatment time.

FIG. 1 is a schematic depiction of an example embodiment of a personal hygiene system 1 in accordance with the present disclosure. FIG. 1 comprises several depictions of optional features, where it shall be clear that these optional features shall not be interpreted as limiting. The personal hygiene system 1 comprises a personal hygiene device 100 and a separate control device 200. Further, a separate instruction element 300 and a distant network unit 400 are shown that are not considered as part of the personal hygiene system 1.

The personal hygiene device 100 here comprises a treatment head 10, which is in particular replaceable, and a handle 20. The treatment head here comprises a treatment element 11 that can be driven into at least an oscillatory rotation M (indicated by a double arrow) around a rotation axis R. The treatment element 11 may be additionally or alternatively be driven into a poking motion A (also indicated by a double arrow) along the direction of the rotation axis R.

The personal hygiene device 100 comprises a receiver unit 110, a control unit 120, and a functional unit 130. Further optional features of the personal hygiene device 100 are shown as well: a transmitter unit 111, a memory unit 125 connected with the control unit 120, a first sensor unit 135 for monitoring a use parameter of the personal hygiene device 100 during operation, two indicator elements 140 and 141, an on/off-switch 150, a mode switch 151 and a display 160. If a transmitter unit 111 is present, the receiver unit 110 and the transmitter unit 111 together may be realized as a transceiver unit.

While the personal hygiene device 100 is here shown as an electric toothbrush, this shall be considered as non-limiting. In particular, the example treatment head 10 is also not to be considered as non-limiting and the treatment head 10 may be realized as not replaceable, the whole treatment head 10 may be driven into a certain movement, which may in particular be different from the movement described before.

The separate control device 200 comprises a transmitter unit 210 and further optional features such as a receiver unit 211, an external interface unit 220 (which may comprise at least one of a reader unit 221, a network connection unit 222, or a user-interface unit 223 or 224), an input element 225 (which may be connected with the external interface unit 220 for triggering a receiving operation), and/or a storage unit 230. If a receiver unit 211 is present, the transmitter unit 210 and the receiver unit 211 together may be realized as a transceiver unit. The user-interface unit 223, 224—if present—may be realized as at least one of a keyboard or array of buttons 223 or touch-sensitive display 224 (on which virtual keys, buttons, sliders etc. may be depicted).

Figure 2:
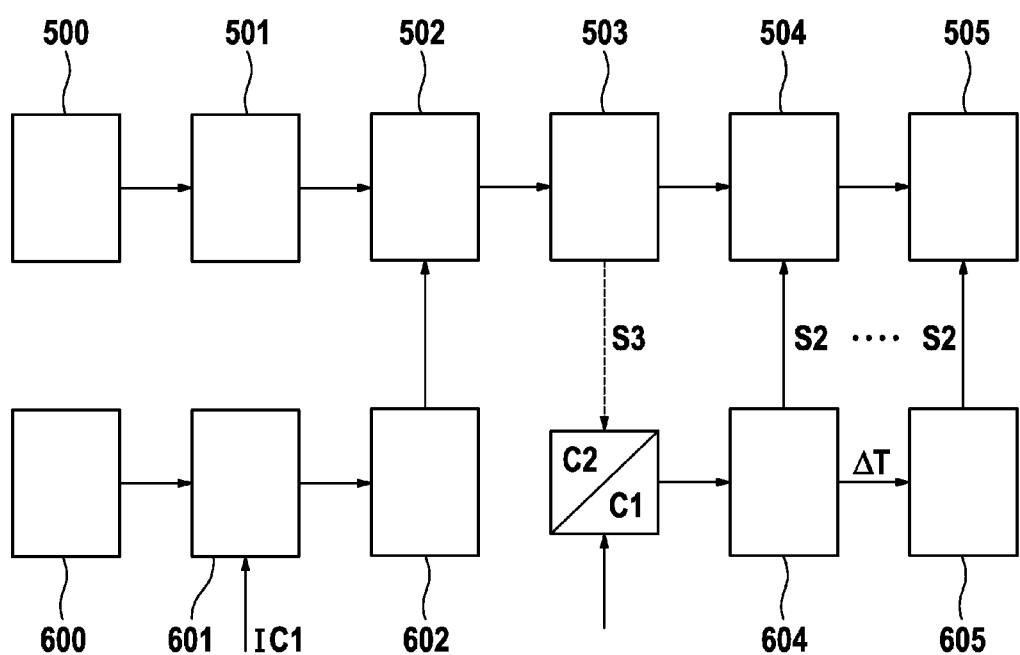
FIG. 2 is a depiction of an example flow of interaction between a separate control device and a personal hygiene device.

By way of an example sequence of activities a possible mode of operation is explained. Reference is also made to FIG. 2, in which the sequence of activities (or: steps) is schematically depicted. Firstly, a personal hygiene device 100 is provided having a control unit that is in a default state in which only a first functional mode can be provided (activity 500 of FIG. 2). Further, a separate control device 200 for at least one-directional communication with the personal hygiene device 100 (where the communication direction goes from the separate control device 200 to the personal hygiene device 100) is provided, which separate control device 200 is in a default control mode (activity 600 in FIG. 2). The separate control device 200 (which is in a default control mode) receives a first instruction command IC1 via an external interface unit 220. E.g. the user may push an input element 225 that triggers a receiving operation of the external interface unit 220 such as an optical reading of a representation of a (portion of a) first instruction command 310 that may be presented to a reader unit 221 by means of a separate instruction element 300 (e.g. a piece of carton onto which the representation of the (portion of the) first instruction command 310 is printed)—see activity 601 of FIG. 2. After having received the first instruction command IC1, the separate control unit 200 compares the first instruction command IC1 with at least one predetermined instruction command assigned to an upgrade of the personal hygiene device 100. If the first instruction command and the predetermined instruction coincide, the separate control device 200 switches from the default control mode into a first control mode. Switching into the first control mode triggers that the separate control device 200 sends a first signal S1 via a transmitter unit 210 to a receiver unit 110 of the personal hygiene device 100 (activity 602 in FIG. 2). The first signal S1 is then received by the receiver unit 110 of the personal hygiene device and forwarded to the control unit 120. The control unit 120 then switches from its default state in which it inhibits that the functional unit 130 provides a second functional mode to a first state in which provision of the second functional mode is enabled (activity 502).

A user may now be able to switch on the personal hygiene device 100 (e.g. using an on/off switch 150) and to choose the second functional mode via a mode switch 151. Additionally and or alternatively, the separate control device 200 may be arranged to consider a first condition C1 as being met when it determines that the personal hygiene device is switched on; switching on of the personal hygiene device 200 may be detected by a sound recognition device that can identify e.g. a typical start sound of the functional unit 130 of the personal hygiene device 200. Once the separate control device 200 considers the first condition C1 as met (and the separate control device 200 is in the first control mode), the separate control device 200 sends a second signal S2 to the personal hygiene device 100 via its transmitter unit 210 (activity 604 in FIG. 2). Once the second signal S2 is received by the receiver unit 110 of the personal hygiene device 100, the control unit 120 may be triggered to unalterably drive the functional unit 130 into one of the available functional modes defined by the second signal S2. E.g., if the upgrade is concerned with a particular treatment, a predetermined sequence of functional modes may be employed for achieving a good treatment result. In order to send a particular sequence of second signals, the separate control device 200 may have a first signal sequence stored in a storage unit 230 from which a consecutive member is send as second signal each time the first condition C1 is met (e.g. each time the personal hygiene device is switched on).

Instead of being recognized by the separate control device 200, the switching-on action may be communicated by the personal hygiene device 100 via a transmitter unit 111 to a receiver unit 211 of the separate control device 200. The personal hygiene device 100 may thus send a third signal S3 when a second condition C2 is met (activity 503). The second condition C2 may be met when the personal hygiene device 100 is moved (e.g. taken away from the sink in the bath room). The personal hygiene device 100 may comprise a movement sensor (e.g. an accelerometer) via which it is sensed that the personal hygiene device 100 is moved and which triggers that the third signal S3 is sent. Or the second condition C2 is considered as met once the personal hygiene device 100 is switched on (which then triggers that the third signal is sent).

In some embodiments, the second signal S2 send by the separate control device 200 to the personal hygiene device 100 has a duration that spans the treatment time AT (activities 504 to 505 and 604 to 605). The second signal S2 may comprise information that is directly used by the control unit 120 for controlling the functional unit 130 to provide the second functional mode (e.g. the mentioned information may be driving information such as pulse width modulation values (e.g. voltage, frequency and duty cycle) allowing the control unit to provide essentially in real time a respective driving signal at a drive unit.

The second signal (or the first signal) may comprise information for being displayed on a display 160 provided at the personal hygiene device or a display 224 provided at the separate control device 200.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene system comprising
a personal hygiene device having a receiver unit, a control unit, and a functional unit; and
a separate control device having a transmitter unit;
wherein the control unit is arranged to drive the functional unit in at least a first functional mode and a second functional mode different from the first functional mode, and the control unit is further arranged to inhibit provision of the second functional mode while the control unit is in a default state;
wherein the transmitter unit of the separate control device is arranged to send at least a first signal to the receiver unit of the personal hygiene device when the separate control device is switched from a default control mode to a first control mode;
wherein the control unit is arranged to be switched from the default state into a first state when the first signal is received by the receiver unit, in which first state the control unit is arranged to permit provision of the second functional mode only during a first allowance period;
wherein the control unit is arranged to inhibit the provision of the first functional mode while the control unit is in the first state; and
wherein at least one of the separate control device and the control unit is arranged to set at least one parameter of at least the second functional mode in dependence on use information of the personal hygiene device.

2. The personal hygiene system in accordance with claim 1, wherein the separate control device comprises an external interface unit for receiving at least a first instruction command and wherein the separate control device is arranged to be switched into the first control mode when the first instruction command coincides with at least one predetermined instruction command.

3. The personal hygiene system in accordance with claim 2, wherein the external interface unit comprises at least one of a reader unit for reading at least a portion of the first instruction command from a separate instruction element; a network connection unit for receiving at least a portion of the first instruction command from a distant network unit such as a network server; or a user-interface unit for receiving user input and for using the user input at least as a portion of the first instruction command.

4. The personal hygiene system in accordance with claim 2, wherein the separate control device comprises an input element that is arranged for receiving user input and for triggering a receiving operation by the external interface unit.

5. The personal hygiene system in accordance with claim 1, further comprising an indicator element for indicating the availability of at least the second functional mode.

6. The personal hygiene system in accordance with claim 1, wherein the separate control device is arranged to send information about the second functional mode enabling the control unit to drive the functional unit into the second mode, wherein the first signal comprises the information being sent.

7. The personal hygiene system in accordance with claim 1, wherein the transmitter unit of the separate control device is arranged to send at least a second signal to the receiver unit of the personal hygiene device when the separate control unit is in the first control mode and a first condition is met, and the control unit is arranged to drive the functional unit into one of the at least first and second functional modes depending on the second signal.

8. The personal hygiene system in accordance with claim 7, wherein the second signal extends over a predefined temporal length, wherein the predefined temporal length coincides with a treatment period during which the functional unit is driven by the control unit.

9. The personal hygiene system in accordance with claim 8, wherein the second signal comprises driving information for driving the functional unit into the second functional mode, and the control unit is arranged for directly using the driving information.

10. The personal hygiene system in accordance with one of claim 7, wherein the personal hygiene device has a transmitter unit arranged for sending at least a third signal to a receiver unit of the separate control device when a second condition is met, wherein the second condition is met when the personal hygiene device is switched on, and wherein the separate control device is arranged to consider the first condition as met when the third signal is received.

11. The personal hygiene system in accordance with claim 1, wherein the separate control device comprises a storage unit for storing at least a first signal sequence, and the transmitter unit of the separate control device is arranged to send consecutive members of the first signal sequence to the personal hygiene device each time when a third condition is met.

12. The personal hygiene system in accordance with claim 1, wherein at least one of the separate control device and the personal hygiene device comprises a display for displaying information in dependence on at least one of the first signal, the second signal, and the current member of the first signal sequence.

13. The personal hygiene system in accordance with claim 1, wherein the personal hygiene system comprises at least a first sensor unit for monitoring at least a first use parameter during at least a portion of a treatment period.

* * * * *